US011608358B2

United States Patent
Ahn et al.

(10) Patent No.: US 11,608,358 B2
(45) Date of Patent: Mar. 21, 2023

(54) METHOD OF PREPARING COMPOSITION CONTAINING FACTOR VIII (FVIII) AND VON WILLEBRAND FACTOR (VWF) WITH CONTROLLED CONTENT OF VON WILLEBRAND FACTOR (VWF)

(71) Applicant: GREEN CROSS HOLDINGS CORPORATION, Gyeonggi-do (KR)

(72) Inventors: Jee Won Ahn, Seoul (KR); Kwan Young Ko, Gyeonggi-do (KR); Jeong Hye Yoon, Gyeonggi-do (KR); Seung-Ho Baek, Gyeonggi-do (KR); Min Jung Kim, Seoul (KR); Geun Hye Yeo, Gyeonggi-do (KR); Jung-Ae Lim, Gyeonggi-do (KR); Soo-kwang Kim, Gyeonggi-do (KR)

(73) Assignee: GREEN CROSS HOLDINGS CORPORATION, Gyeonggi-Do (KR)

( * ) Notice: Subject to any disclaimer, the term of this patent is extended or adjusted under 35 U.S.C. 154(b) by 468 days.

(21) Appl. No.: 16/758,386

(22) PCT Filed: Oct. 26, 2018

(86) PCT No.: PCT/KR2018/012820
§ 371 (c)(1),
(2) Date: Apr. 22, 2020

(87) PCT Pub. No.: WO2019/083319
PCT Pub. Date: May 2, 2019

(65) Prior Publication Data
US 2020/0247843 A1 Aug. 6, 2020

(30) Foreign Application Priority Data
Oct. 27, 2017 (KR) .................. 10-2017-0141444

(51) Int. Cl.
*C07K 1/18* (2006.01)
*A61K 38/37* (2006.01)
*B01D 15/00* (2006.01)
*B01D 15/36* (2006.01)

(52) U.S. Cl.
CPC .............. *C07K 1/18* (2013.01); *A61K 38/37* (2013.01); *B01D 15/362* (2013.01); *B01D 15/363* (2013.01)

(58) Field of Classification Search
CPC ........ C07K 1/18; A61K 38/37; B01D 15/362; B01D 15/363
See application file for complete search history.

(56) References Cited

U.S. PATENT DOCUMENTS

| 4,361,509 A | 11/1982 | Zimmerman et al. |
| 4,764,369 A | 8/1988 | Neurath et al. |

FOREIGN PATENT DOCUMENTS

| EP | 0600480 A2 | 6/1994 |
| EP | 0934747 A1 | 10/1998 |
| EP | 0934748 B1 | 10/2005 |
| KR | 20100058520 A | 6/2010 |
| WO | WO2010082184 A1 | 7/2010 |
| WO | WO2015021423 A2 | 2/2015 |
| WO | WO2016162310 A1 | 10/2016 |

OTHER PUBLICATIONS

Batlle, J., et al., "Von Willebrand factor/factor VIII concentrates in the treatment of von Willebrand disease", Blood Coagulation and Fibrinolysis, 2009, pp. 89-100, vol. 20, Publisher: Lippincott Williams & Wilkins.
Castaman, G., "Treatment of von Willeband disease with FVIII/ VWF concentrates", Blood Transfus, 2011, pp. s9-s13; DOI 10.2450/ 2011.003S, vol. 9.
Josic, DJ, et al., "Purification of factorVIII and von Willebrand factor from human plasma by anion-exchange chromatography", Journal of Chromatography B, 1994, pp. 181-194, vol. 662, Publisher: Elsevier.
Austen, D., "The Chromatographic Separation of Factor VIII on Aminohexyl Sepharose", "British Journal of Hematology", 1979, pp. 669-674, vol. 43.
Fuddenham, E., et al., "The Properties of Factor VIII Coagulant Activity Prepared by Immunoadsorbent Chromatography", "Journal of Laboratory Clinical Medicine", 1979, pp. 40-53, vol. 93, No. 1.

*Primary Examiner* — Sikarl A Witherspoon
(74) *Attorney, Agent, or Firm* — Hultqvist, PLLC; Steven J. Hultquist (57) ABSTRACT

Disclosed is a method for preparing a composition comprising factor VIII (FVIII) and von Willebrand factor (vWF), wherein the content of the von Willebrand factor (vWF) can be controlled by mixing the factor VIII (FVIII) with the von Willebrand factor (vWF) at an appropriate ratio after separately purifying the factor VIII (FVIII) and the von Willebrand factor (vWF) from plasma in a single process. The method can prepare and purify a composition comprising factor VIII (FVIII) and a varying content of von Willebrand factor (vWF) without increasing the amount of impurities other than the von Willebrand factor (vWF) compared to a method of purifying factor VIII (FVIII) separately, without significantly increasing the processing time (within 3 hours) compared to a method of purifying factor VIII (FVIII), and without changing the yield of factor VIII (FVIII).

15 Claims, 6 Drawing Sheets

M: Marker
Lane 1 : Dissolution
Lane 3 : AEX load
Lane 5 : AEX elution
Lane 7 : CEX unadsorbed liquid
Lane 9 : CEX elution Lane 2 : Cold precipitation and centrifuge
Lane 4 : AEX unadsorbed liquid
Lane 6 : CEX load
Lane 8 : CEX wash

METHOD OF PREPARING COMPOSITION CONTAINING FACTOR VIII (FVIII) AND VON WILLEBRAND FACTOR (VWF) WITH CONTROLLED CONTENT OF VON WILLEBRAND FACTOR (VWF)

CROSS-REFERENCE TO RELATED APPLICATIONS

This application is a U.S. national phase under the provisions of 35 U.S.C. § 371 of International Patent Application No. PCT/KR18/12820 filed Oct. 26, 2018, which in turn claims priority of Korean Patent Application No. 10-2017-0141444 filed Oct. 27, 2017. The disclosures of International Patent Application No. PCT/KR18/12820 and Korean Patent Application No. 10-2017-0141444 are hereby incorporated herein by reference in their respective entireties, for all purposes.

TECHNICAL FIELD

The present invention relates to a method of preparing a composition comprising factor VIII (FVIII) and von Willebrand factor (vWF), wherein the content of the von Willebrand factor (vWF) can be controlled and, more specifically, to a method for preparing a composition comprising factor VIII (FVIII) and von Willebrand factor (vWF) wherein the content of the von Willebrand factor (vWF) can be controlled by separately purifying the factor VIII (FVIII) and the von Willebrand factor (vWF) from plasma in a single process and mixing the factor VIII (FVIII) with the von Willebrand factor (vWF) at an appropriate ratio.

BACKGROUND ART

The anti-hemophilia factor (factor VIII) is a protein coenzyme that has the function of facilitating the formation of fibrin clots by promoting the activity of factor X during blood clotting. Factor VIII corrects defects of blood clotting in the plasma of hemophilia patients and circulates in the plasma in the form of a complex with von Willebrand factor (hereinafter referred to as "vWF").

vWF is a protein that can change the defects of platelet functions in von Willebrand deficiency and forms a complex with factor VIII. vWF is a hemostatic factor which is produced in vascular endothelial cells or bone marrow megakaryocytes and present as a multimeric structure (having a molecular weight of 500 to 20,000 kDa) in which a single subunit including 2050 amino acid residues (monomer having a molecular weight of about 250 kDa) is linked via a disulfide bond. The concentration of vWF in the blood is about 10 µg/ml, and as the molecular weight thereof increases, inactivity thereof increases. vWF has two major functions as a hemostatic factor. One is the function as a carrier protein that stabilizes the blood-clotting factor VIII by binding thereto and the other is the function of forming a thrombus by adhering platelets to tissues in the vascular endothelial cells of the injured vascular wall and aggregating the same.

A part of the factor VIII/von Willebrand complex having blood-clotting activity is called "factor VIII clotting protein", "VIII clotting activity", or simply "factor VIII:C", and other part having the activity of correcting defects in platelet function in von Willebrand deficiency is referred to as "factor-VIII-related antigen", "VIII:Ag", "VIII:RP factor", or "vWF". This complex is formed via a non-covalent bond and may be divided into two proteins, each having its own characteristics under appropriate conditions.

Recent clinical SIPPET research results have shown that FVIII/VWF products have a lower incidence of immunogenicity in hemophilia A patients than products obtained by purifying FVIII alone at high purity.

In order to determine the medicinal value of the blood-clotting activity resulting from factor VIII:C and the structures of the complex VIII:C/vWF, factor VIII:C, and vWF, many attempts have been made to separate, purify and concentrate the factor VIII:C and vWF. The methods used for this are generally based on immunoadsorption or ion exchange chromatography and are not applied industrially due to the problem therewith in which it is difficult to detach the target protein or recover the protein having the same activity from a charged ionic material without affecting the activity of the protein.

Tuddenham et al. reported a method for separating factor VIII:C from vWF using immunoadsorption chromatography (see: E. G. D. Tuddenham et al., Journal of Laboratory Clinical Medicine, 93:40 (1979)). That is, factor VIII:C is separated from vWF and other plasma proteins using chromatography using a column packed with agarose beads bound with multivalent antiserum against vWF (anti-vWF). Plasma containing VIII:C/vWF is made to pass through a column on which both VIII:C and vWF are adsorbed, undesired plasma proteins are removed from the column by washing with buffer, and the desired factor VIII:C is then obtained by eluting with calcium ions. Although this method realizes improved purity and efficiency of factor VIII:C, the final product still contains vWF and other plasma proteins. These impurities are considered to be due to the use of multivalent antiserum that binds to agarose beads. Since most immunoglobulins that constitute antiserum are not specific for vWF, the degree of binding of vWF-specific antibodies to agarose is relatively low due to competition with other types of antibodies. For this reason, the final product is often contaminated with other plasma proteins.

Austin et al. also reported a method for separating factor VIII:C from vWF and ristocetin cofactors through chromatography using a column packed with aminohexyl-substituted agarose. (see: D. E. G. Austen, British Journal of Haematology, 43:669 (1979)). This method is improved with regard to human and swine VIII:C/vWF complexes, but has a problem in that the final product still includes impurities.

The methods by both Tuddenham et al. and Austin et al. have disadvantages in that the concentration of the final purified product is low and a large amount of impurities is contained in the final product.

Furthermore, Zimmerman et al. reported a method for separating high-purity factor VIII:C at a high concentration from vWF using two-step purification (see: U.S. Pat. No. 4,361,509). That is, the first step is immunoadsorption of the factor VIII:C contained in the plasma and the concentrate, and the adsorbent used therefor is a vWF-specific monoclonal antibody having an appropriate medium such as agarose beads bound thereto. The monoclonal antibody used herein is obtained by producing a monoclonal antibody from the ascites of the mouse and then purifying the same. Plasma containing VIII:C/vWF is made to pass through a column packed with an electro-adsorbent, so that VIII:C/vWF is first adsorbed, unadsorbed proteins are removed from the column by washing with a buffer, and only the adsorbed factor VIII:C is eluted by treating with a calcium-containing solution. The vWF moiety remains adsorbed to the anti-vWF monoclonal antibody bound to the medium. The factor VIII:C thus recovered is highly pure and almost completely free of impurities, but the concentration thereof is, disadvantageously, too low for use in medicine. Thus, the second step of this process is concentration of the purified factor VIII:C using affinity chromatography. About 10 to 20 IU (international unit) of the VIII:C factor-containing solution obtained in the first step is injected into a column packed with aminohexyl-substituted agarose and washed sufficiently with a buffer solution, and then a calcium-ion-containing solution is injected into the column to elute the factor VIII:C with a concentration of at least 1,000 units/ml, which corresponds to an at least 160,000-fold concentration of plasma. However, in accordance with this purification method, the anti-vWF monoclonal antibody (produced from the ascites of the mouse) bound to the medium is detached upon elution of factor VIII:C, and the final eluate contains a mouse-derived protein, that is, an anti-vWF monoclonal antibody. Thus, this method has a problem in that the eluate is not suitable for administration to a human subject in need of factor VIII:C.

To date, in the process for purifying the factor VIII/von Willebrand complex, the content of von Willebrand factor cannot be controlled as desired while maintaining a high yield of 40 to 60% unless factor VIII is artificially discarded. There has been reported no process capable of reducing the content of impurities other than von Willebrand factor compared to before the control.

Accordingly, there is a need for the development of a new purification method capable of separating and purifying a complex including factor VIII and vWF bound at an appropriate ratio at high concentration by controlling the content of vWF while minimizing the contamination of impurities.

In this circumstance, the present inventors have found that the content of vWF can be controlled by performing two elution processes using anion exchange chromatography and one additional elution process using cation exchange chromatography and mixing the eluate obtained during each elution in one process at a desired ratio, if necessary, in the process of separating and purifying the factor VIII and vWF from plasma, and thus a composition having a vWF content and a content ratio of the factor VIII and vWF, which are artificially controlled, can be separated and purified at high purity and high concentration. Based on this finding, the present invention has been completed.

DISCLOSURE

Technical Problem

It is one object of the present invention to provide a method of preparing a composition containing factor VIII/von Willebrand factor (FVIII/vWF) and having a varying content of the von Willebrand factor (vWF), without causing a change in the yield of the factor VIII.

Technical Solution

In accordance with one aspect of the present invention, the above and other objects can be accomplished by the provision of a method of preparing a composition comprising factor VIII and von Willebrand factor (FVIII/vWF) with a controlled content of the von Willebrand factor (vWF), the method comprising:

(a) obtaining a primary eluate using a first elution buffer by performing anion exchange chromatography on a plasma sample isolated from a human body;

(b) obtaining an eluate by performing cation exchange chromatography on the primary eluate;

(c) obtaining an eluate by applying a second elution buffer to a column used to obtain the primary eluate through the anion exchange chromatography of step (a); and (d) mixing the eluate of the cation exchange chromatography obtained in step (b) with the secondary eluate of the anion exchange chromatography obtained in step (c).

In another aspect of the present invention, provided is a pharmaceutical composition for treating a blood-clotting disorder comprising, as an active ingredient, a composition comprising factor VIII and von Willebrand factor (FVIII/vWF) prepared by the method.

In another aspect of the present invention, provided is a method of treating a blood-clotting disorder comprising administering the composition to a patient with a blood-clotting disorder.

In another aspect of the present invention, provided is the use of the composition for the preparation of a drug for treating a blood-clotting disorder.

BEST MODE

Unless defined otherwise, all technical and scientific terms used herein have the same meanings as appreciated by those skilled in the field to which the present invention pertains. In general, the nomenclature used herein is well-known in the art and is ordinarily used.

The present invention is based on the finding that, by performing two elution processes using anion exchange chromatography and one additional elution process using cation exchange chromatography and mixing the eluate obtained during each elution in one process at a desired ratio, if necessary, in the process of separating and purifying the factor VIII and von Willebrand factor (vWF) from plasma, the loss of the von Willebrand factor (vWF) during anion exchange chromatography can be alleviated and the content of the vWF can be controlled, and the complex of factor VIII (FVIII) and vWF, having a controlled vWF content, can be separated and purified at high purity and high concentration.

Thus, in one aspect, the present invention relates to a method of preparing a composition comprising factor VIII/von Willebrand factor (FVIII/vWF), with a controlled content of the von Willebrand factor (vWF).

The method may comprise:

(a) obtaining a primary eluate using a first elution buffer by performing anion exchange chromatography on a plasma sample isolated from a human body;

(b) obtaining an eluate by performing cation exchange chromatography on the primary eluate;

(c) obtaining a secondary eluate by applying a second elution buffer to a column used to obtain the primary eluate through the anion exchange chromatography of step (a) to; and (d) mixing the eluate of the cation exchange chromatography obtained in step (b) with the secondary eluate of the anion exchange chromatography obtained in step (c).

The plasma sample isolated from the human body in the present invention may be obtained by a method including: (i) freezing the plasma sample isolated from the human body, dissolving the resulting precipitate, forming a cold precipitate and removing impurities; and (ii) sterilizing the product of step (i) through treatment with a detergent.

In the present invention, the factor VIII (FVIII) and von Willebrand factor (vWF) can be purified from the plasma sample isolated from the human body, and additionally, in order to extract the factor VIII (FVIII) and von Willebrand factor (vWF) present in the frozen plasma precipitate, in the step of dissolving the frozen plasma precipitate, the frozen plasma precipitate is added to the extract and then dissolved at a temperature of 23 to 27° C. for 3 to 5 hours while stirring at 200 to 300 rpm and.

In the present invention, the frozen plasma precipitate is dissolved in an extracting solution containing heparin 1.5±0.5 IU/cryopaste kg (green cross, sodium heparinate, Cat. No. 50-1341-7), ethanol 1±0.5%/cryopaste kg (Korean alcohol, Cat. No. 40000533), and water for injection 3 L/cryopaste kg, but this extracting solution may be replaced with an extracting solution commonly used in the art. When unfrozen serum is used, the step of dissolving the precipitate may be modified to be suitable for the unfrozen serum.

In order to remove vitamin-K-dependent proteins such as FII, FVII, FIX and FX, an aluminum hydroxide gel is added to the dissolved precipitate to form a cold precipitate. Specifically, the dissolved precipitate is stirred at 22 to 28° C. and at 200 to 300 rpm for 5 to 10 minutes, the pH is adjusted to 6.1 to 6.6, and the dissolved precipitate is slowly allowed to cool to a temperature of 10 to 14° C. over a period of 30 minutes to 90 minutes to form a cold precipitate. The aluminum hydroxide gel added is preferably 150 to 250 g of a formulation of a 1 to 3% aluminum hydroxide gel suspension per 1 kg of the frozen plasma precipitate, but the amount may be appropriately added or subtracted depending on the state of the plasma precipitate.

In order to remove the aluminum hydroxide gel and impurities, the cold precipitate is applied to a centrifuge at a input rate of 5 to 7 L/min and centrifuged at a rate of 3,000 rpm or more and at a constant temperature of 10 to 14° C., and the centrifuged solution is collected by clarification-filtration.

The product of step (i) is sterilized by treatment with a detergent. In this case, the solvent and detergent may be used without limitation, as long as they can inactivate viruses, particularly lipid-enveloped viruses. The detergent may be selected from the group consisting of nonionic and ionic detergents, and is preferably substantially unmodified. In particular, in view of ease of removal, a nonionic detergent is preferred, and tri-n-butyl phosphate (TNBP), as disclosed in U.S. Pat. No. 4,764,369, is most preferred as the solvent, but the present invention is not limited thereto.

The virus-inactivating agent particularly preferable for implementing the present invention is a mixture of one or more selected from TNBP and polysorbate 80 (Tween 80), Triton X-100 and Triton X-45, but is not limited thereto.

A preferred detergent mixture is added such that the concentration of TNBP in the clarified solution is within the range of 0.2 to 0.6% by weight, specifically 0.24 to 0.36% by weight, and the concentration of polysorbate 80 is within the range of 0.6 to 1.5% by weight, specifically, 0.8 to 1.2% by weight.

The detergent mixture is treated under conditions capable of forming a solution substantially free of risk from viral activity by inactivating lipid-enveloped viruses. The reaction temperature in the above conditions is specifically to 30° C., more specifically 19 to 28° C., and most specifically 26 to 27° C., the reaction time is specifically 1 to 24 hours, more specifically 4 to 12 hours, and most specifically about 5 to 7 hours, and the detergent mixture is preferably treated while slowly stirring the same at 40 to 80 rpm.

Toyopearl DEAE 650M resin is used as an anion exchange resin in the anion exchange chromatography of step (a), and a $Na^+$-controlling liquid is added such that the $Na^+$ concentration of the detergent-treated solution is adjusted to 120 to 150 mmol/L, the pH is adjusted to 6.8 to 7.2, and the detergent-treated solution is applied into the column at a flow rate of 80 to 120 cm/hour and adsorbed onto the resin. Then, re-equilibration is performed by applying a re-equilibration buffer in an amount of 4 to 6 times the volume of the column at a flow rate of 80 to 120 cm/hour, and then a primary eluate is eluted by applying a first elution buffer in an amount of 4 to 6 times the volume of the column at a flow rate of 80 to 120 cm/hour. The first elution buffer contains 150 to 170 mM NaCl, 8 to 12 mM Na-citrate.$H_2O$, 100 to 140 mM glycine and 0.5 to 1.5 mM $CaCl_2.2H_2O$, and the pH can be specifically adjusted to 6.6 to 7.4, more specifically, the pH can be adjusted to 6.8 to 7.2, and most specifically, the pH can be adjusted to 6.9 to 7.1.

SP Sepharose resin is used as a cation exchange resin in the cation exchange chromatography of step (b), and the primary eluate is applied into the column at a flow rate of 180 to 200 cm/hour and adsorbed onto the resin. Then, an elution buffer is applied into the column onto which the primary eluate adsorbed in an amount of 4 to 6 times the volume of the column at a flow rate of 230 to 270 cm/hour to elute an eluate. The elution buffer to obtain the eluate through cation exchange chromatography contains 380 to 420 mM NaCl, 8 to 12 mM Na-citrate.$H_2O$, 100 to 140 mM glycine and 0.5 to 1.5 mM $CaCl_2.2H_2O$, and the pH can be specifically adjusted to 6.0 to 7.0, more specifically, the pH can be adjusted to 6.3 to 6.7, and most specifically, the pH can be adjusted to 6.4 to 6.6.

Then, in step (c), a second elution buffer is applied applied in an amount of 2 to 4 times the volume of the column into the column used for obtaining the primary eluate at a flow rate of 30 to 60 cm/hour to elute a secondary eluate. The second elution buffer contains 230 to 270 mM NaCl, 8 to 12 mM Na-citrate.$H_2O$, 100 to 140 mM glycine and 0.5 to 1.5 mM $CaCl_2.2H_2O$, and the pH can be specifically adjusted to 6.6 to 7.4, more specifically, the pH can be adjusted to 6.8 to 7.2, and most specifically, the pH can be adjusted to 6.9 to 7.1.

In the present invention, the steps (b) and (c) may be performed simultaneously, or may be performed in an appropriately changed order. Meanwhile, the eluate of the anion exchange chromatography of step (a) may contain a mixture of the factor VIII and vWF, the eluate of the cation exchange chromatography of step (b) may contain vWF, and the factor VIII is present in an amount of 0.01% by weight or less. The eluate of the cation exchange chromatography of step (b) and the secondary eluate of the anion exchange chromatography of step (c) may be mixed in a volume ratio of 9:1 to 1:9.

The anion exchange resin used herein may be substituted with a diethylaminoethyl (DEAE) or quaternary ammonium group, but is not limited thereto. Specifically, either an anion exchange resin having a strongly basic quaternary ammonium group or a weakly basic diethylaminoethyl (DEAE) group may be selected and used.

For example, the strongly basic anion exchange resin includes, but is not limited to, Q Sepharose Fast Flow, Q Sepharose High Performance, Resource Q, Source 15Q, Source 30Q, Mono Q, Mini Q, Capto Q, Capto Q ImpRes, Q HyperCel, Q-Ceramic HyperD F, Nuvia Q, UNOsphere Q, Macro-prep high Q, Macro-prep 25 Q, Fractogel EMD TMAE (S), Fractogel EMD TMAE Hicap (M), Fractogel EMD TMAE (M), Eshmuno Q, Toyopearl QAE-550C, Toyopearl SuperQ-650C, Toyopearl GigaCap Q-650M, Toyopearl Q-600C AR, Toyopearl SuperQ-650M, Toyopearl SuperQ-650S, TSKgel SuperQ-5PW (30), TSKgel SuperQ-5PW (20), TSKgel SuperQ-5PW, and the like, but any other strongly basic anion exchange resin known in the art may be used. In addition, the example of the weakly basic anion exchange resin includes, but is not limited to, Toyopearl DEAE, DEAE Sepharose Fast Flow, Eshmuno Q, Fractogel EMD DEAE and the like, and any other weakly basic anion exchange resin known in the art may be used. More specifically, the anion exchange chromatography may be carried out using an anion exchange chromatography resin selected from the group consisting of Toyopearl DEAE, Q Sepharose Fast Flow, DEAE Sepharose Fast Flow, Mono Q, Capto Q, Fractogel EMD TMAE (M), Eshmuno Q, Toyopearl GigaCap Q-650M and Fractogel EMD DEAE.

The appropriate volume of resin used for the anion exchange chromatography is determined based on the column dimensions, i.e., the diameter of the column and the height of the resin, and depends, for example, on the amount of immunoglobulin solution in the solution that is applied and the binding performance of the resin that is used. Prior to anion exchange chromatography, the anion exchange resin is specifically equilibrated with a buffer to allow the resin to bind to a counter ion thereof.

In the present invention, Toyopearl DEAE 650M resin is used as the anion exchange resin, and any equalibration buffer, wash buffer and elution buffer known in the art, such as sodium phosphate buffer, citric acid buffer or acetic acid buffer, may be used as the column buffer.

In the present invention, the cation exchange resin may be Sephadex, Sepharose, HyperCel, Source, SP Sepharose, SP Sepharose Fast Flow, Fractogel EMD SO3 or the like, but is not limited thereto, and any cation exchange resin known in the art may be used. In one embodiment of the present invention, SP Sepharose resin is used as the cation exchange resin. Meanwhile, any equalibration buffer, wash buffer and elution buffer known in the art, such as sodium phosphate buffer, citric acid buffer or acetic acid buffer, may be used as the column buffer.

In step (d) of the present invention, the eluate of the cation exchange chromatography obtained in step (b) and the secondary eluate of the anion exchange chromatography obtained in step (c) are mixed, and the titer of factor VIII (FVIII) and von Willebrand factor (vWF) is 1:0.6 to 1:1.4, specifically 1:1. In this case, the titer of the factor VIII (FVIII) and the von Willebrand factor (vWF) in the primary eluate and the secondary eluate, and the titer of the von Willebrand factor (vWF) in the eluate (the eluate obtained after cation exchange chromatography) are measured to determine the degree of mixing.

In the present invention, the method may further comprise, after the step (d), (e) concentrating the mixed solution such that the concentration of the factor VIII (FVIII) is adjusted to 125 IU/mL or more; and (f) adding the secondary eluate obtained in step (c) to further control the titer of the factor VIII (FVIII) and the von Willebrand factor (vWF).

In the step (e), the mixture is concentrated and microfiltered. In the present invention, the mixture is concentrated using a 100 kDa cut-off size ( ) membrane made of cellulose acetate. In the present invention, the factor VIII (FVIII) is preferably concentrated to a concentration of 125 IU/mL or more.

In step (f), the secondary eluate obtained in step (c) may be added to further control the titer of the factor VIII (FVIII) and the von Willebrand factor (vWF). At this time, the titer of the factor VIII (FVIII) and the von Willebrand factor (vWF) is controlled depending on the amount of the secondary eluate that is added.

After controlling the titer of the factor VIII (FVIII) and the von Willebrand factor (vWF), the formulation is prepared by applying a formulation buffer. The formulation buffer contains 8.9 to 9.1 mg/mL of glycine, 2.8 to 3.2 mg/mL of Na-citrate.$2H_2O$, 0.1 to 0.2 mg/mL of $CaCl_2.2H_2O$, 20 to 30 mg/mL of sucrose, and 1.0 to 1.5 mg/mL of Polysorbate 80.

Meanwhile, in each step of the present invention, microfiltration is appropriately performed so that the factor VIII (FVIII) and the von Willebrand factor (vWF) can be purified with high purity.

In still another aspect, the present invention relates to a pharmaceutical composition for treating a blood-clotting disorder comprising, as an active ingredient, a composition comprising factor VIII and von Willebrand factor (FVIII/vWF) prepared by the method.

In the present invention, the titer of the factor VIII (FVIII) and the von Willebrand factor (vWF) may be 1:0.2 to 1:3.0, preferably 1:0.6 to 1:2.8, but is not limited thereto.

The blood-clotting disorder may be hemophilia A or von Willebrand deficiency, but is not limited thereto.

The pharmaceutical composition according to the present invention may further contain a pharmaceutically acceptable carrier.

The pharmaceutically acceptable carrier contained in the pharmaceutical composition may include a pharmaceutically acceptable carrier commonly used in the preparation, such as lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methylhydroxybenzoate, propylhydroxy benzoate, talc, magnesium stearate, mineral oil and the like. The pharmaceutical composition may further contain a lubricant, a wetting agent, a sweetener, a flavoring agent, an emulsifier, a suspending agent, a preservative, or the like, in addition to the ingredients described above.

The composition may be prepared into a unit dose form, or may be incorporated into a multi-dose container through formulation using a pharmaceutically acceptable carrier and excipient according to an ordinary method. In this case, the formulation may be in the form of a solution in an oil or aqueous medium, a suspension, a syrup or an emulsion, or may be in the form of an extract, a powder, a granule, a tablet or a capsule. The composition may further contain a dispersant or a stabilizer. In addition, the composition may be administered alone as a single therapeutic agent or in combination with another therapeutic agent. In this case, the composition of the present invention may be administered sequentially or simultaneously with a conventional therapeutic agent.

In another aspect, the present invention provides a method of treating a blood-clotting disorder comprising administering the composition to a patient with a blood-clotting disorder.

The composition according to the present invention may be administered to a subject through a variety of routes and a dosage depending on the condition of the patient and the presence of side effects, and the optimum administration method and dosage may be selected within an appropriate range by those skilled in the art. In addition, the composition may be administered in combination with other drugs or physiologically active substances, the therapeutic effect of which is known for the disease to be treated, or may be formulated as a combination with other drugs.

In another aspect, the present invention provides the use of the composition for the preparation of a drug for treating a blood-clotting disorder.

Hereinafter, the present invention will be described in more detail with reference to examples. However, it will be obvious to those skilled in the art that these examples are provided only for illustration of the present invention and should not be construed as limiting the scope of the present invention.

EXAMPLE 1: PROCESS OF PURIFYING FACTOR VIII/VON WILLEBRAND (FVIII/VWF) COMPLEX 1-1. Precipitate Dissolution The plasma-frozen cryoprecipitate was added to an extraction buffer (containing heparin 1.5±0.5 IU/cryopaste kg (Green Cross, Sodium Heparin, Cat. No. 50-1341-7), ethanol 1±0.5%/cryopaste kg (Korean alcohol) and water for injection 3 L/ cryopaste kg) and dissolved at 25±1° C. for 4 hours after addition of the cryoprecipitate while stirring at 250 rpm, and then the pH was adjusted to 7.1±0.1.

1-2. Cold Precipitation/Centrifugation

A suspension (200 g/cryopaste kg) of 2% aluminum hydroxide gel [Al(OH)$_3$ gel, Brenntag, Cat. No. A1090S] was added to the dissolved precipitate solution and stirred at 250 rpm and at 24 to 26° C. for 5 to 10 minutes. After adjusting the pH to 6.3 to 6.4, the temperature of the liquid was gradually dropped to 10 to 13° C. for 60 minutes to form a cold precipitate. After adjusting the rotation speed of a centrifuge (GEA, BKB45) to 5,400 rpm, centrifugation was performed by applying the cold precipitate into the centrifuge at a input rate of 5 to 7 L/min while maintaining the temperature at 10 to 14° C. The centrifuged solution was collected by clarifying filtration through a 2.0/1.2 µm filter (Merck Millipore, PolySep II).

1-3. Pretreatment with Solvent/Detergent (S/D)

The temperature of the liquid that had undergone the clarifying filtration was adjusted to 26 to 27° C., and the pH was adjusted to 6.9 to 7.1. While stirring the pH-adjusted solution at 350 rpm, an inactivation solution was added for 20 minutes to 60 minutes such that tri-n-butyl phosphate (TNBP) (Merck Millipore, Cat. No. 1.00002) and polysorbate (J. T. Baker, Cat. No. 4117) were present in amounts of 0.3±0.06% and 1.0±0.2%, respectively, and the solution was then further stirred for 30 minutes. The stirred solution was collected by microfiltration through a 0.45/0.2 µm filter (Sartorius, Sartobran P).

1-4. Treatment with Solvent/Detergent (S/D)

The S/D pretreated solution was inactivated at 26 to 27° C. for 5 to 7 hours while slowly stirring at 40 to 80 rpm.

1-5. Anion Exchange Chromatography Process

Toyopearl DEAE 650M resin (Tosoh, Cat. No. 0007974) was packed into a column to a height of 23±2 cm. A Na$^+$-controlling liquid was added such that the concentration of Na$^+$ in the S/D treated solution was 135±13.5 mmol/L, and the pH was adjusted to 6.9 to 7.1. The pH-adjusted solution was subjected to clarifying filtration and then injected into a column and adsorbed at a flow rate of 100 cm/hour. After adsorption, re-equilibration was performed by flowing 4 to 6 CV of a re-equilibration buffer (120 mM NaCl, 10 mM Na-citrate.2H$_2$O, 120 mM glycine, pH 7.0±0.1) at a flow rate of 100 cm/hour. After re-equilibration, primary elution was performed by flowing 4 to 6 CV of a first elution buffer (160 mM NaCl, 10 mM Na-citrate.2H$_2$O, 120 mM glycine, 1 mM CaCl$_2$.2H$_2$O, pH 7.0±0.1) at a flow rate of 100 cm/hour. After the primary elution, secondary elution was performed by flowing 3 CV of a second elution buffer (250 mM NaCl, 10 mM Na-citrate.2H$_2$O, 120 mM glycine, 1 mM CaCl$_2$.2H$_2$O, pH 7.0±0.1) at a flow rate of 45 cm/hour.

1-6. Cation Exchange Chromatography Process

SP Sepharose resin (GE, Cat. No. 17-0729) was packed into a column to a height of 17±1.7 cm. The primary eluate collected through anion exchange chromatography was collected by microfiltration through a 0.45/0.2 um filter (Sartorius, Sartobran P). The micro-filtered solution was applied into a column and adsorbed at a flow rate of 200 cm/hour. After adsorption, washing was performed by flowing 5 CV of a wash buffer (260 mM NaCl, 10 mM Na-citrate.2H$_2$O, 120 mM glycine, 1 mM CaCl$_2$.2H$_2$O, pH 6.5±0.1) at a flow rate of 250 cm/hour. After washing, elution was performed by flowing 5 CV of a elution buffer(400 mM NaCl, 10 mM Na-citrate.2H$_2$O, 120 mM glycine, 1 mM CaCl$_2$.2H$_2$O, pH: 6.5±0.1) at a flow rate of 250 cm/hour. The collected eluate (tertiary eluate) was mixed with CEX equilibration buffer (10 mM Na-citrate.2H$_2$O, 120 mM glycine, 1 mM CaCl$_2$.2H$_2$O, pH 6.5±0.1) in an amount of 0.6 times the volume of the eluate.

1-7. Analysis of Titer of FVIII Activity 1-7-1. Standard Preparation

The standard (NIBSC, blood-clotting factor VIII:C concentrate, human (07/350) or standard equivalent thereto) was diluted to 1.0 IU/mL in an FVIII-deficient plasma (Siemens, Cat. No. OTXW100) and then diluted 5-, 10-, 20-and 40-fold with CA system buffer (Siemens, Cat. No. B4265-35) containing 1% albumin.

1-7-2. Sample Preparation

Each sample was diluted to 1.0 IU/mL of factor VIII with FVIII-deficient plasma (Siemens, Cat. No. OTXW100) and then diluted 16-, 18-, 20- and 22-fold with CA system buffer containing 1% albumin.

1-7-3. Titer Measurement

The time taken for clotting of the standard and sample was measured using a coagulometer (Merlin medical, MC10 Plus) to analyze the activated partial thromboplastin time (aPTT).

When the percentage (%) of the time taken for the sample to clot with respect to the time taken for the standard to clot was obtained, the titer value of the sample was obtained using the following Equation:

Equation) titer value of sample (IU/mL)=Sample measurement result (%)×dilution factor (fold)× 0.002 (correction factor)×standard titer (IU/mL)

1-8. vWF Addition

The collected secondary eluate of anion exchange chromatography and the diluted eluate (tertiary eluate) of cation exchange chromatography were subjected to process inspection, and a mix solution prepared by mixing FVIII and vWF in a total titer ratio of 1:1 was collected by microfiltration through a 0.45/0.2 um filter (Sartorius, Sartobran P).

1-9. Concentration and Microfiltration

The vWF added solution was concentrated to adjust the FVIII concentration to 125 IU/mL or more using a 100 kDa cut-off size 100 kDa membrane (Sartorius, Hydrosart) made of cellulose acetate. The concentrated solution was collected by microfiltration through a 0.45/0.2 um filter (Sartorius, Sartobran P), which was used as a stock fraction.

1-10. Titer Adjustment

The titer of FVIII was adjusted to 125 IU/mL through the addition of anion exchange chromatography second elution buffer (250 mM NaCl, 10 mM Na-citrate.$2H_2O$, 120 mM glycine, 1 mM $CaCl_2$.$2H_2O$, pH 7.0±0.1).

1-11. Formulation

The titer and $Na^+$ concentration were adjusted to 100 IU/mL and 200±50 mM, respectively, through the addition of a formulation buffer (8.97 mg/mL of glycine, 2.936 mg/mL of Na-citrate.$2H_2O$, 0.16 mg/mL of $CaCl_2$.$2H_2O$, 25.0 mg/mL of sucrose, and 1.25 mg/mL of Polysorbate 80).

1-12. Sterile Filtration

The filtrate collected by sterile filtration through a 0.45/0.2 um filter (Sartorius, Sartobran P) was used as a final stock solution and refrigerated until filling.

The overall process is summarized in Table 1 below.

TABLE 1

| Process name | Process conditions | | Object |
|---|---|---|---|
| Precipitate dissolution | Temperature: 25 ± 1° C. Dissolution time: 4 hours Amount of added EtOH: 1 ± 0.1%/cryopaste g Heparin: 1.5 ± 0.5 IU/cryopaste g | | Extraction of Factor VIII and vWF present in cryopaste |
| Adsorption with aluminum hydroxide gel | Temperature: 25 ± 1° C. pH: 7.1 ± 0.1 Al(OH)$_3$ gel: 0.2 g/cryopaste g Al(OH)$_3$ gel treatment time: 7.5 ± 2.5 minutes | | Removal of impurities (vitamin-K-dependent proteins such as F II, FVII, FIX, F X) |
| Cold precipitation/ centrifugation | pH: 6.35 ± 0.05 Temperature: 11.5 ± 1.0° C. | | Removal of aluminum hydroxide gel and impurities |
| S/D treatment | 0.3% TNBP in filtrate, 1% polysorbate 80 in filtrate Temperature: 26.5 ± 0.5° C. pH: 7.0 ± 0.1 S/D addition, stirring for 30 minutes and then reaction for 6 ± 1 hr (incubation) | | Viral inactivation |
| Anion exchange chromatography | AEX load | Sample: Solution obtained by S/D reaction and then 1.2 um filtration pH: 7.0 ± 0.1 $Na^+$ concentration adjustment: 135 ± 13.5 mmol/L Linear flow rate: 100 cm/hour | Removal of S/D ingredients and impurities, high-purity FVIII purification |
| | Equilibration | pH: 7.0 ± 0.1 NaCl: 120 mM Na-citrate•$2H_2O$: 10 mM Glycine: 120 mM $Na^+$ concentration: 135 ± 13.5 mmol/L Linear flow rate: 100 cm/hour CV: 5 ± 1 CV | |
| | Washing | pH: 7.0 ± 0.1 NaCl: 160 mM Na-citrate•$2H_2O$: 10 mM Glycine: 120 mM | |

TABLE 1-continued

| Process name | | Process conditions | Object |
|---|---|---|---|
| | Elution | CaCl$_2$•2H$_2$O: 1 mM<br>Na$_+$ concentration:<br>175 ± 17.5 mmol/L<br>Linear flow rate: 100 cm/hour<br>CV: 5.0 ± 0.5 CV<br>pH: 7.0 ± 0.1<br>NaCl: 250 mM<br>Na-citrate•2H$_2$O: 10 mM<br>Glycine: 120 mM<br>CaCl$_2$ (2H$_2$O): 1 mM<br>Na$^+$ concentration:<br>265 ± 26.5 mmol/L<br>Linear flow rate: 45 cm/hour<br>CV: 2 CV | |
| Cation exchange chromatography | CEX load | Sample: solution obtained by AEX elution 1 and 0.2 um filtration<br>pH: 7.0 ± 0.1<br>Linear flow rate: 200 cm/hour | Impurity removal, high-purity vWF purification |
| | Washing | pH: 6.5 ± 0.1<br>NaCl: 260 mM<br>Na-citrate•2H$_2$O: 10 mM<br>Glycine: 120 mM<br>CaCl$_2$ (2H$_2$O): 1 mM<br>Na$^+$ concentration:<br>275 ± 27.5 mmol/L<br>linear flow rate: 250 cm/hour<br>CV: 5CV | |
| | Elution | pH: 6.5 ± 0.1<br>NaCl: 400 mM<br>Na-citrate•2H$_2$O: 10 mM<br>Glycine: 120 mM<br>CaCl$_2$ (2H$_2$O): 1 mM<br>Na$^+$ concentration:<br>420 ± 42.0 mmol/L<br>linear flow rate: 250 cm/hour<br>CV: 3CV | |
| vWF addition | | AEX elution 2 + CEX elution + CEX equilibration buffer (CEX volume × 0.6)<br>CEX equilibration buffer<br>pH: 6.5 ± 0.1<br>Na-citrate•2H$_2$O: 10 mM<br>Glycine: 120 mM<br>CaCl$_2$ (2H$_2$O): 1 mM<br>FVIII, vW F titer of AEX eluate and vW F titer of CEX eluate are measured before mixing | mixing |
| Concentration | | 100 kDa membrane, TMP 0.2~0.3 bar<br>Concentration fold: 10~33 fold | Concentration |

EXAMPLE 2: DETERMINATION OF REMOVAL BEHAVIORS OF MAJOR IMPURITIES DURING PURIFICATION PROCESS

Removal behaviors of fibrinogen, fibronectin, FII, FX, IgA and IgM present as major impurities in each step of the process were determined.

The removal behaviors of all of fibrinogen, fibronectin, FII, FX, IgA and IgM were determined by ELISA. The detailed experimental method is as follows.

Fibrinogen content was tested using a commercially available human fibrinogen ELISA kit (manufactured by Assaypro, Cat. No. EF1040-1) in accordance with the manual provided by the kit manufacturer.

Fibronectin content was tested using a commercially available human fibronectin ELISA kit (manufactured by Assaypro, Cat. No. EF1045-1) in accordance with the manual provided by the kit manufacturer.

FII content was tested using a commercially available human prothrombin ELISA kit (manufactured by Assaypro, Cat. No. EP3023-1) in accordance with the manual provided by the kit manufacturer.

FX content was tested using a commercially available human fibrinogen ELISA kit (manufactured by Assaypro, Cat. No. EF1010-1) in accordance with the manual provided by the kit manufacturer.

IgA content was tested using a commercially available human IgA ELISA quantitation set (manufactured by Bethyl, Cat. No. E80-102) and an ELISA Starter Accessory Kit (manufactured by Bethyl, Cat. No. E101) in accordance with the manual provided by the kit manufacturer.

IgM content was tested using a commercially available human IgM ELISA quantitation set (manufactured by Bethyl, Cat. No. E80-102) and an ELISA Starter Accessory Kit (manufactured by Bethyl, Cat. No. E101) in accordance with the manual provided by the kit manufacturer.

Figure 1:
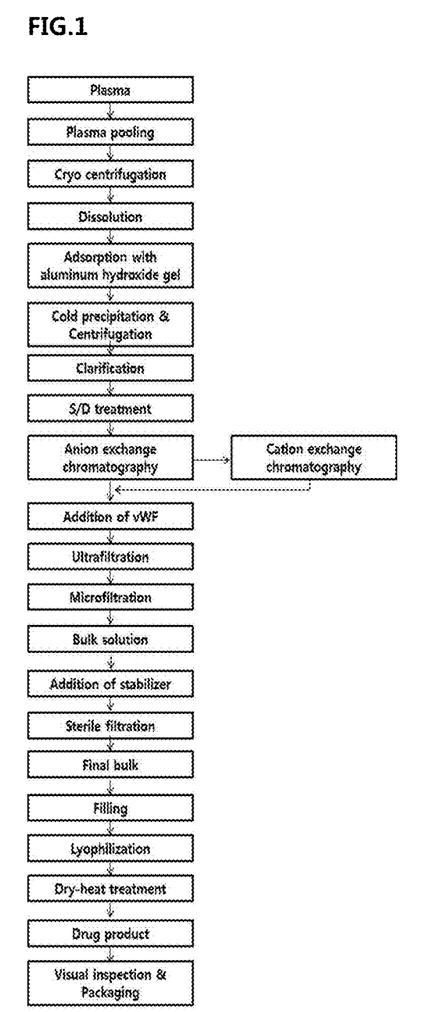
FIG. 1 is a flowchart showing a process of preparing a composition comprising factor VIII (FVIII) and von Willebrand factor (vWF) according to the present invention.
Figure 2:
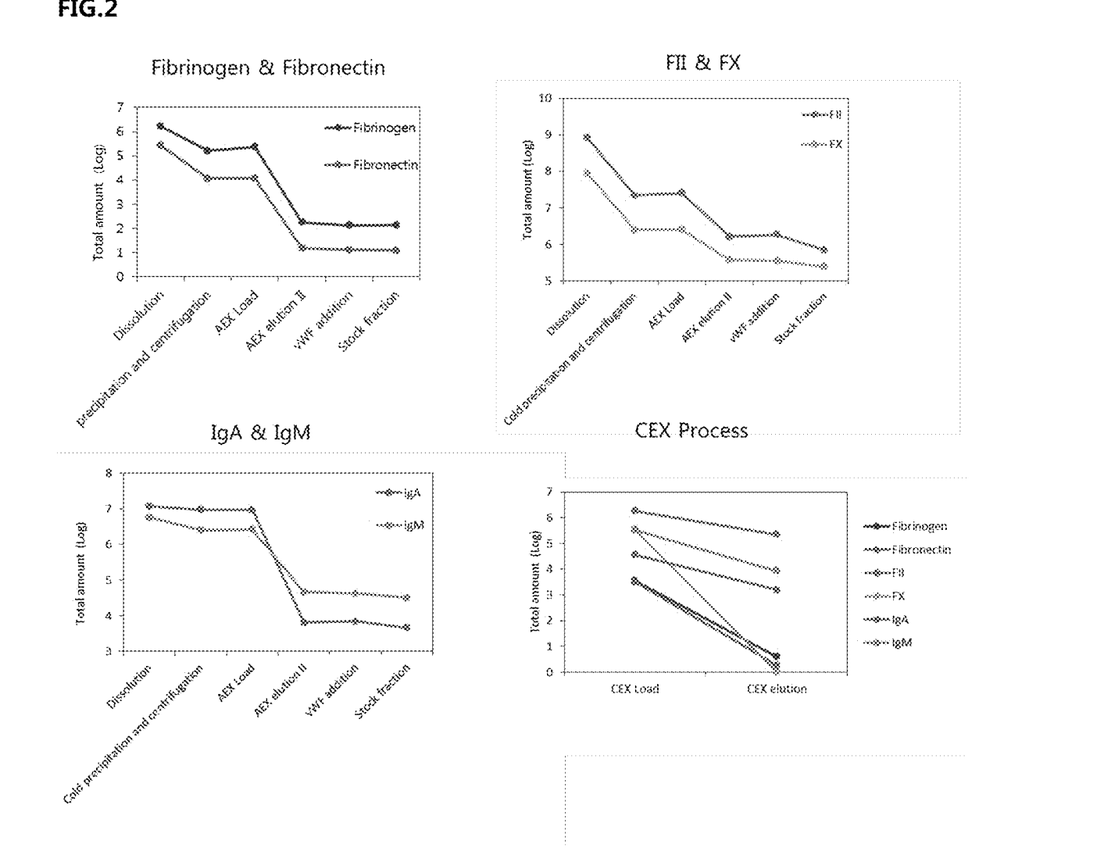
FIG. 2 shows the removal behavior of fibrinogen, fibronectin, FII, FX, IgA and IgM, as main impurities in the process according to the present invention.

The result showed that 90.6% of fibrinogen was removed after cold precipitation and centrifugation processes and 99.9% or more of fibrinogen was removed after the AEX process, and that 95.9% of fibronectin was removed after cold precipitation and centrifugation processes and 99.9% or more of fibronectin was removed after the AEX process. This indicates that fibrinogen and fibronectin were mainly removed through cold precipitation and centrifugation. In addition, 97.4% of FII and 97.3% of FX were removed after cold precipitation and centrifugation. Then, 93.6% of FII and 85.1% of FX were removed after the AEX process. From the dissolution process to the AEX process, 99.8% of FII and 99.6% of FX were removed and the majority of FII and FX were removed by cold precipitation and centrifugation. Meanwhile, the majority of IgA and IgM were removed during the AEX process, unlike the four kinds of impurities. The removal rates of IgA and IgM after cold precipitation and centrifugation were relatively low, 18.9% and 55.6%, respectively, but 99.9% of IgA and 99.2% of IgM were removed after AEX. That is, it was found that IgA and IgM were mainly removed through the AEX process. 99.9% or more of fibrinogen, fibronectin and FX contained in the CEX load solution was removed through the CEX process. 95.6% of IgA and 97.4% of IgM were removed but only 87.7% of FII was removed, which is lower than the removal of the other impurities (FIG. 2).

The analysis showed that the removal of major impurities such as fibrinogen, fibronectin, FII and FX during the cold precipitation and centrifugation processes and the removal of IgA and IgM during the AEX process are important in determining quality. In addition, the analysis showed that some impurities remaining in the AEX primary eluate were removed through the CEX process, and the amounts of residual impurities according to the process of the present invention are shown in Table 2 below. As can be seen from the following table, the levels of impurities that may affect the safety of the purified product are equal to or higher than those of conventional products.

Figure 4:
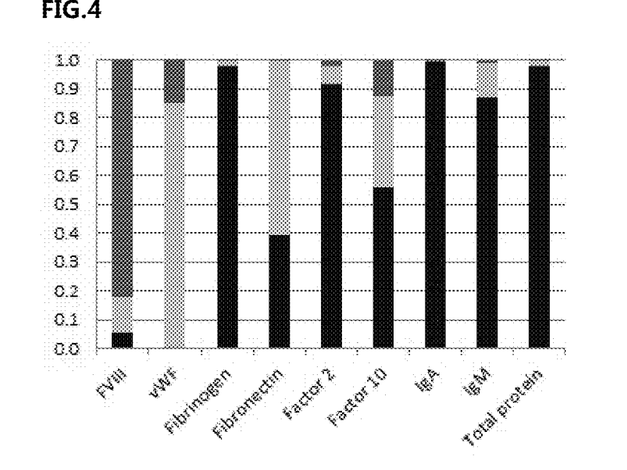
FIG. 4 shows the protein distribution in the anion exchange chromatography step in the process according to the invention, wherein the black rectangles represent a column-loading step, the light gray rectangles represent a column-washing step, and the dark gray rectangles represent a column elution step.

4, the result showed that the sample loaded into the AEX column had a vWF (IU) content more than 2 times the FVIII (IU) content, but the final eluate had a vWF (IU) content of only 0.4 times the FVIII (IU) content, which indicates that a large amount of vWF was lost in the AEX washing step (FIG. 4).

EXAMPLE 5: ANALYSIS OF FVIII TITER RECOVERY IN ANION EXCHANGE CHROMATOGRAPHY PROCESS STEP

The recovery rate of titer of FVIII in the AEX process step was determined. As can be seen from Table 3, the result of analysis of three batches showed that the FVIII titer recovery rate was 85% in the AEX process, and the discarded FVIII in the unadsorbed and washed liquids during the column process was about 15% of the load.

TABLE 3

| AEX process | FVIII mass balance |
| --- | --- |
| Load | 100 ± 2 |
| Unadsorbed liquid | 4 ± 1 |
| Washed liquid (CEX load) | 11 ± 2 |
| Eluate | 85 ± 10 |

TABLE 2

| Analysis item | Batch 1 | Batch 2 | Batch 3 | Batch 4 | Green Eight | Immunate | Octanate | Fahndi | Wilate |
| --- | --- | --- | --- | --- | --- | --- | --- | --- | --- |
| Fibronectin (μg/FVIII IU) | 0.1 | 0.1 | 0.1 | 0.1 | 2.5 | 0.4 | 0.5 | 0.4 | 0.8 |
| Fibrinogen (μg/FVIII IU) | 1.8 | 1.0 | 1.5 | 1.7 | 4.7 | 0.5 | 2.0 | 0.3 | 1.7 |
| F II (μg/FVIII IU) | 0.02 | 0.01 | 0.01 | <0.01 | | | | | |
| F X (μg/FVIII IU) | <0.01 | <0.01 | <0.01 | <0.01 | | | | | |
| IgA (μg/FVIII IU) | 0.06 | 0.03 | 0.05 | 0.06 | 0.10 | 0.10 | <0.01 | 0.01 | 0.01 |
| IgM (μg/FVIII IU) | 0.2 | 0.3 | 0.4 | 0.3 | 1.1 | 0.1 | 0.2 | 0.1 | 0.2 |

EXAMPLE 3: SDS-PAGE [NON-REDUCING CONDITION] ANALYSIS OF PROCESS PRODUCT OBTAINED DURING EACH STEP

SDS-PAGE analysis was performed on the product obtained during each process step. Each sample was diluted to 7.5 ug/well with non-reducing loading buffer and loaded in 3 to 8% Tris-acetate gel and electrophoresis was performed at 100 V for 90 minutes.

Figure 3:
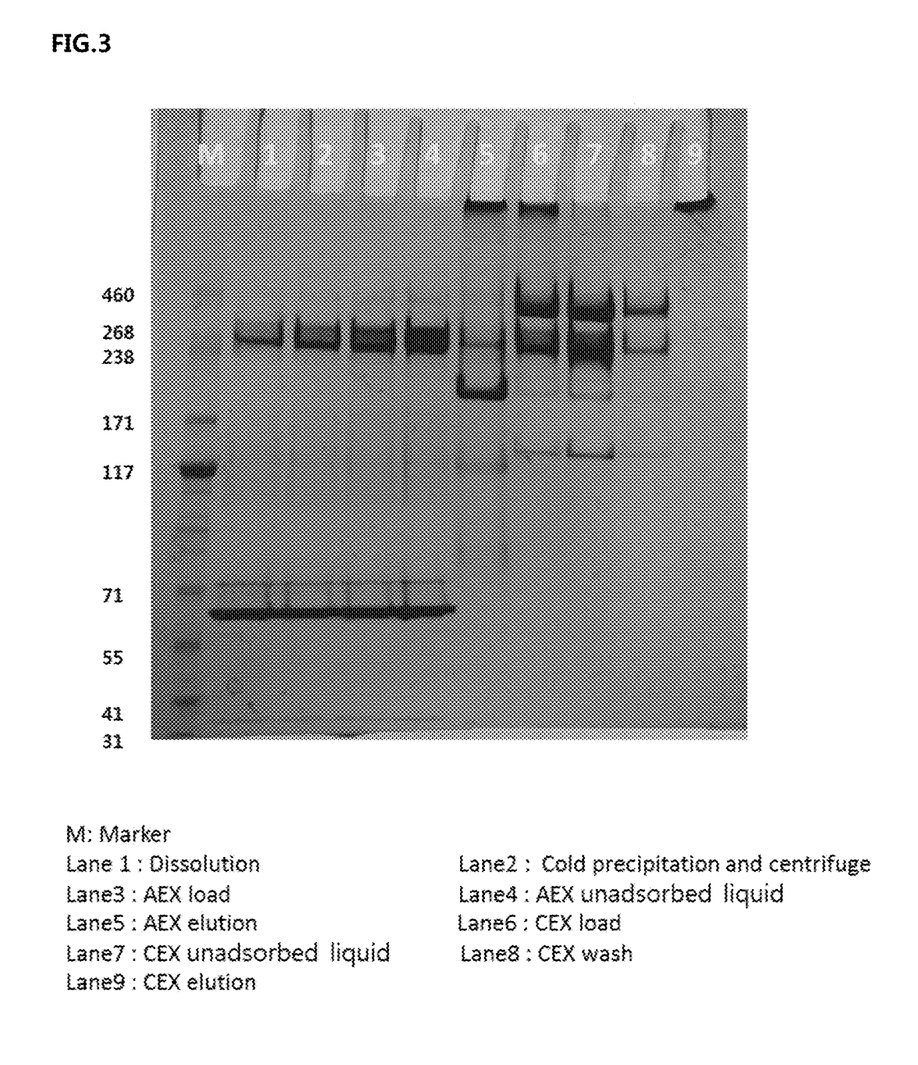
FIG. 3 shows the result of SDS-PAGE analysis of products obtained during respective steps in the process according to the present invention.

The result showed that impurities of 70 kDa or less and impurities of 230 to 270 kDa were removed during the AEX column process. It was found that the CEX column process was efficient for purifying only multimeric vWF of 460 kDa or more at high purity (FIG. 3).

EXAMPLE 4: VWF LOSS DURING ANION EXCHANGE CHROMATOGRAPHY PROCESS STEP

The intermediate of each step during the AEX process used for FVIII purification was analyzed. As shown in FIG.

Figure 5:
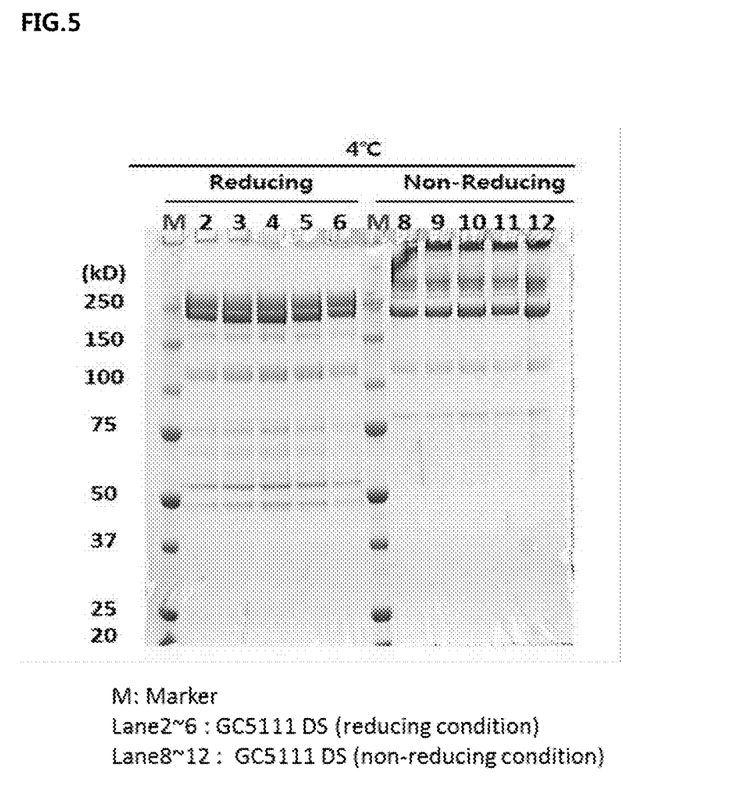
FIG. 5 shows the result of SDS-PAGE analysis of a product obtained by mixing an AEX eluate with a CEX eluate followed by concentration, in the process according to the present invention.

EXAMPLE 6: CHARACTERIZATION BY ADDITION OF CATION EXCHANGE CHROMATOGRAPHY ELUATE 6-1. Recovery of vWF Loss The AEX eluate and the CEX eluate were mixed and concentrated, and then each sample was diluted in the same amount of a reducing loading buffer and a non-reducing loading buffer and loaded on a 4-12% Bis-Tris gel, and electrophoresis was performed at 120 V for 90 minutes. The result showed that a product with an improved vWF ratio could be obtained (FIG. 5).

When the CEX eluate was mixed with the AEX eluate, the ratio of vWF:Rco/FVIII:OS was higher than the ratio of vWF:Rco/FVIII:OS purified through the AEX process (Table 4), which indicates that the vWF content increased more than two times after mixing than before mixing.

Meanwhile, the impurity content ratio to the FVIII (IU) was found to be unchanged before and after mixing the CEX eluate, which is considered to be due to effective removal of the impurities during the CEX process. Meanwhile, the result of comparison in the FVIII activity between before and after mixing the CEX eluate showed that the activity of FVIII after mixing was similar to or higher than that before mixing (Table 4).

TABLE 4

| Impurities | Content | |
|---|---|---|
| | Before mixing | After mixing |
| vWF:Rco/FVIII:OS (IU/IU) | 0.44 ± 0.01 | 0.93 ± 0.05 |
| Fibrinogen (ug/FVIII IU) | 1.57 ± 0.60 | 1.34 ± 0.31 |
| Fibronectin (ug/FVIII IU) | 0.27 ± 0.17 | 0.16 ± 0.05 |
| Factor 2 (ug/FVIII IU) | ≤0.02 | ≤0.02 |
| Factor 10 (ug/FVIII IU) | ≤0.01 | ≤0.01 |
| IgA (ug/FVIII IU) | 0.06 ± 0.00 | 0.07 ± 0.03 |
| IgM (ug/FVIII IU) | 0.34 ± 0.09 | 0.30 ± 0.07 |
| FVIII specific activity (mg/FVIII IU) | 62.94 ± 7.04 | 68.40 ± 7.02 |

6-2. Characterization of Final Product

The results of the precise analysis in three batches regarding the properties of the final product are shown in Table 5, and there was no difference between the vWF:Rco/FVIII:OS ratio and the vWF:Rco/FVIII:CS ratio. Therefore, it was found that when the final bulk solution was filled into the vial after controlling a FVIII content in order to produce hemophilia A products, the both FVIII:OS and FVIII: CS , could be easily used for FVIII activity measurement. The residual content of impurities derived from cryoprecipitate and of process-related impurities such as heparin and aluminum were all measured as very low values.

Meanwhile, the vWF:Rco/vWF:Ag ratio is about 0.9, which suggests that the final product forms a high-molecular-weight multimer (HMWM), thereby being very effective in promoting aggregation of platelets. HMWM is known to be very effective in the treatment of mucosal bleeding, and the concentration of vWF:Rco/vWF:Ag effective for VWD treatment is known to be 0.7 or more.

TABLE 5

| Category | Test item | | Result |
|---|---|---|---|
| Biological property | FVIII activity (IU/mL) | One stage method(OS) | 100.9 ± 5.3 |
| | | Chromogenic method(CS) | 92.2 ± 5.3 |
| | vWF activity (IU/mL) | vWF:Rco | 93.5 ± 6.4 |
| | | vWF:Ag | 107.7 ± 13.9 |
| | Specific activity of FVIII:OS (IU/mg) | | 68.9 ± 2.7 |
| | vWF:Rco/vWF:Ag (IU/IU) | | 0.9 ± 0.1 |
| | vWF:Rco/FVIII:OS (IU/IU) | | 0.9 ± 0.1 |
| | vWF:Rco/FVIII:CS (IU/IU) | | 1.0 ± 0.0 |
| Impurity | Fibrinogen (μg/mL) | | 132.1 ± 2.4 |
| | Fibronectin (μg/mL) | | <39.0 |
| | Coagulation factor II (μg/mL) | | 0.16 ± 0.08 |
| | Coagulation factor X (ng/mL) | | 0.27 ± 0.02 |
| | IgA (μg/mL) | | 0.23 ± 0.04 |
| | IgM (μg/mL) | | 0.58 ± 0.12 |
| | IgG (μg/mL) | | 4.4 ± 0.3 |
| | Heparin (IU/mL) | | <0.65 |
| | Aluminum (ppb) | | 38.5 ± 6.9 |

Figure 6:
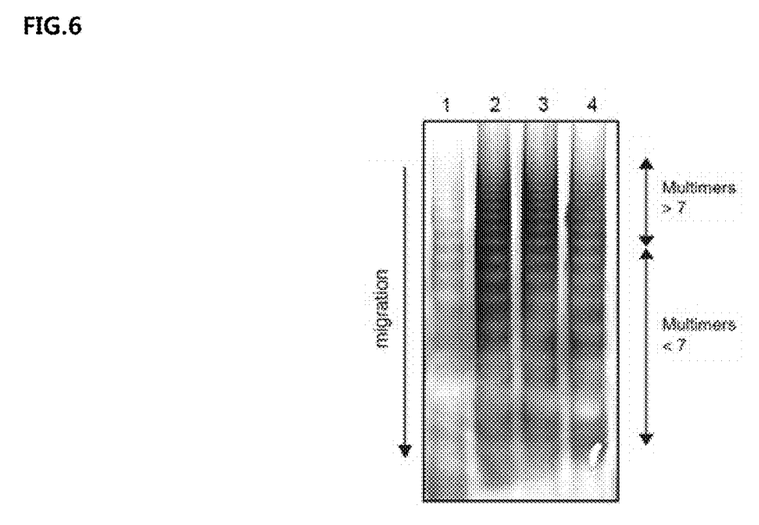
FIG. 6 shows the result of comparison in vWF multimeric patterns between standard human plasma (lane 1) and three purified product batches (lanes 2, 3 and 4) according to the present invention.

The vWF multimer pattern was found to be similar to that of normal plasma containing rich high-molecular-weight multimers (FIG. 6). This means that the addition of purified vWF to low-ratio vWF:Rco/FVIII:C can yield products containing high-molecular-weight vWF multimers.

Figure 7:
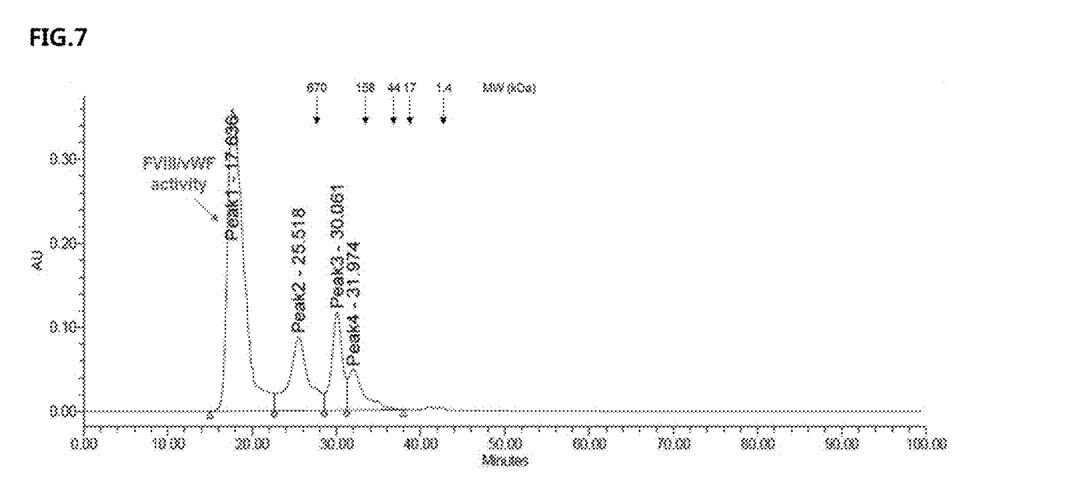
FIG. 7 shows the result of size exclusion chromatography, measured at 280 nm, of the product according to the present invention.

The result of size exclusion chromatography analysis of whether FVIII forms a complex with vWF revealed four major peaks (FIG. 7). The results of fractionation of each peak and analysis of FVIII and vWF activity of each fraction showed that the peak 1 of 670 kDa or more exhibits not only vWF activity but also FVIII activity, and that the other three small-sized peaks exhibit neither vWF activity nor FVIII activity. Taking into consideration the fact that the size of FVIII is about 270 kDa, it can be seen that most FVIII is present in the form of a stable complex in combination with vWF.

EXAMPLE 7: PURIFICATION OF PRODUCT HAVING CONTROLLED MIXING RATIO OF FVIII AND VWF

Concentrated FVIII and vWF coexist in the AEX eluate of Example 1, and vWF is present in the CEX eluate (see FIG. 3, Lane 5 and Lane 9). In this case, the ratio of FVIII and vWF can be adjusted depending on the mixing ratio of AEX eluate and CEX eluate. The following Table 6 shows that the ratio of FVIII and vWF is adjusted according to the mixing ratio of the AEX eluate and the CEX eluate, and that there is almost no change in the content of the major impurities per unit of the titer of FVIII, even when the mixing ratio is adjusted.

TABLE 6

| Batch # | Sample name | FVIII (IU/mL) | vWF (IU/mL) | vWF/FVIII Ratio | Fibrinogen (ug/FVIII IU) | Fibronectin (ug/FVIII IU) | FXI ELISA (ug/FVIII IU) | FX ELISA (ug/FVIII IU) | IgA (ELISA) (ug/FVIII IU) | IgM (ELISA) (ug/FVIII IU) |
|---|---|---|---|---|---|---|---|---|---|---|
| 1 | AEX eluate | 23.4 | 8.4 | 0.4 | 0.8 | 0.2 | 1.1 | 0.6 | 0.1 | 0.5 |
| | CEX eluate | — | 44.7 | — | | | | | | |
| | AEX eluate 60% + CEX eluate 40% mix | 21.8 | 16.7 | 0.8 | 0.6 | 0.2 | 0.9 | 0.7 | 0.0 | 0.3 |
| | AEX eluate 20% + CEX eluate 80% mix | 19.9 | 19.6 | 1.0 | 0.7 | 0.3 | 0.9 | 0.5 | 0.0 | 0.2 |
| 2 | AEX eluate | 33.2 | 11.6 | 0.3 | 0.7 | 0.3 | 0.7 | 0.3 | 0.0 | 0.2 |
| | CEX eluate | — | 44.7 | — | | | | | | |
| | AEX eluate 60% + CEX eluate 40% mix | 27.8 | 19.8 | 0.7 | 0.6 | 0.3 | 0.8 | 0.5 | 0.0 | 0.2 |

TABLE 6-continued

| Batch # | Sample name | FVIII (IU/mL) | vWF (IU/mL) | vWF/FVIII Ratio | Fibrinogen (ug/FVIII IU) | Fibronectin (ug/FVIII IU) | FXI ELISA (ug/FVIII IU) | FX ELISA (ug/FVIII IU) | IgA (ELISA) (ug/FVIII IU) | IgM (ELISA) (ug/FVIII IU) |
|---|---|---|---|---|---|---|---|---|---|---|
| | AEX eluate 20% + CEX eluate 80% mix | 25.7 | 26.8 | 1.0 | 0.4 | 0.2 | 0.7 | 0.5 | 0.0 | 0.2 |

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The present invention has an effect of preparing a composition comprising factor VIII (FVIII) and a varying content of von Willebrand factor (vWF) i) without increasing the amount of impurities other than the von Willebrand factor (vWF), compared to a separately purified product of factor VIII (FVIII), ii) without significantly increasing the processing time (within 3 hours) compared to a separate purification process of factor VIII (FVIII), and iii) without changing the yield of the factor VIII (FVIII).

The invention claimed is:

1. A method of preparing a composition comprising factor VIII (FVIII) and von Willebrand factor (vWF) with a controlled content of the von Willebrand factor (vWF), the method comprising:
   (a) obtaining a primary eluate using a first elution buffer by performing anion exchange chromatography on a plasma sample isolated from a human body;
   (b) obtaining an eluate by performing cation exchange chromatography on the primary eluate;
   (c) obtaining a secondary eluate by applying a second elution buffer to a column used to obtain the primary eluate through the anion exchange chromatography of step (a); and
   (d) mixing the eluate of the cation exchange chromatography obtained in step (b) with the secondary eluate of the anion exchange chromatography obtained in step (c).

2. The method according to claim 1, wherein the primary eluate of the anion exchange chromatography of step (a) comprises a mixture of factor VIII and vWF, and the eluate of the cation exchange chromatography of step (b) comprises vWF and 0.01% by weight or less of the factor VIII.

3. The method according to claim 1, wherein the eluate of the cation exchange chromatography of step (b) and the secondary eluate of the anion exchange chromatography of step (c) are mixed in a volume ratio of 9:1 to 1:9.

4. The method according to claim 1, wherein the first elution buffer comprises 140 to 170 mM NaCl, 8 to 12 mM Na-citrate·H$_2$O, 100 to 140 mM glycine and 0.5 to 1.5 mM CaCl$_2$·2H$_2$O, and has a pH of 6.8 to 7.2.

5. The method according to claim 1, wherein the first elution buffer is applied in an amount of 4 to 6 times a volume of the column at a flow rate of 80 to 120 cm/hour to elute the primary eluate.

6. The method according to claim 1, wherein the second elution buffer comprises 230 to 270 mM NaCl, 8 to 12 mM Na-citrate·H$_2$O, 100 to 140 mM glycine and 0.5 to 1.5 mM CaCl$_2$·2H$_2$O, and has a pH of 6.8 to 7.2.

7. The method according to claim 1, wherein the second elution buffer is applied in an amount of 2 to 4 times the volume of the column at a flow rate of 30 to 60 cm/hour to elute the secondary eluate.

8. The method according to claim 1, wherein the eluate of step (b) is obtained using an elution buffer comprising 380 to 420 mM NaCl, 8 to 12 mM Na-citrate·H$_2$O, 100 to 140 mM glycine and 0.5 to 1.5 mM CaCl$_2$·2H$_2$O, and having a pH of 6.3 to 6.7.

9. The method according to claim 1, wherein the eluate of step (b) is obtained by applying an elution buffer in an amount of 4 to 6 times the volume of the column at a flow rate of 230 to 270 cm/hour.

10. The method according to claim 1, wherein the plasma sample isolated from the human body is obtained by a method comprising:
    (i) freezing the plasma sample isolated from the human body, dissolving a resulting precipitate, forming a cold precipitate and removing impurities; and
    (ii) sterilizing the product of step (i) through treatment with a detergent.

11. The method according to claim 10, wherein the step (a) is carried out by adding a Na$^+$-controlling liquid such that a Na$^+$ concentration of a detergent-treated solution is adjusted to 120 to 150 mmol/L, adjusting a pH to 6.8 to 7.2, and applying the detergent-treated solution into the column at a flow rate of 80 to 120 cm/hour to adsorb the detergent-treated solution.

12. The method according to claim 11, wherein step (a) further comprises perform re-equilibration by applying a re-equilibration buffer in an amount of 4 to 6 times the volume of the column at a flow rate of 80 to 120 cm/hour.

13. The method according to claim 12, wherein the re-equilibration buffer comprises 80 to 120 mM NaCl, 8 to 12 mM Na-citrate·H$_2$O and 100 to 140 mM glycine, and has a pH of 6.8 to 7.2.

14. The method according to claim 1, wherein step (d) comprises mixing the secondary eluate obtained in step (c) with the eluate obtained in step (b) such that a titer of the factor VIII (FVIII) and the von Willebrand factor (vWF) is adjusted to 1:0.2 to 1:3.0.

15. The method according to claim 1, wherein the method further comprises, after step (d):
    (e) concentrating the mixed solution such that the concentration of the factor VIII (FVIII) is adjusted to 125 IU/mL or more; and
    (f) adding the secondary eluate obtained in step (c) to further control the titer of the factor VIII (FVIII) and the von Willebrand factor (vWF).

* * * * *

UNITED STATES PATENT AND TRADEMARK OFFICE
CERTIFICATE OF CORRECTION

PATENT NO. : 11,608,358 B2
APPLICATION NO. : 16/758386
DATED : March 21, 2023
INVENTOR(S) : Jee Won Ahn et al.

It is certified that error appears in the above-identified patent and that said Letters Patent is hereby corrected as shown below:

In the Specification

Column 6, Line 20, "specifically to" should be -- specifically 4 to --.
Column 6, Line 39, "Na-citrate.H$_2$O" should be -- Na-citrate·H$_2$O --.
Column 6, Line 40, "CaCl$_2$.2H$_2$O" should be -- CaCl$_2$·2H$_2$O --.
Column 6, Line 53, "Na-citrate.H$_2$O" should be -- Na-citrate·H$_2$O --.
Column 6, Line 54, "CaCl$_2$.2H$_2$O" should be -- CaCl$_2$·2H$_2$O --.
Column 6, Line 63, "Na-citrate.H$_2$O" should be -- Na-citrate·H$_2$O --.
Column 6, Line 64, "CaCl$_2$.2H$_2$O" should be -- CaCl$_2$·2H$_2$O --.
Column 7, Line 28, "SuperQ-6505" should be -- SuperQ-650S --.
Column 8, Line 32, "Na-citrate.2H$_2$O" should be -- Na-citrate·2H$_2$O --.
Column 8, Line 33, "CaCl$_2$.2H$_2$O" should be -- CaCl$_2$·2H$_2$O --.
Column 10, Lines 4-5, "polysorbate" should be -- polysorbate 80 --.
Column 10, Line 28, "Na-citrate.2H$_2$O" should be -- Na-citrate·2H$_2$O --.
Column 10, Line 32, "Na-citrate.2H$_2$O" should be -- Na-citrate·2H$_2$O --.
Column 10, Line 32, "CaCl$_2$.2H$_2$O" should be -- CaCl$_2$·2H$_2$O --.
Column 10, Line 36, "Na-citrate.2H$_2$O" should be -- Na-citrate·2H$_2$O --.
Column 10, Line 36, "CaCl$_2$.2H$_2$O" should be -- CaCl$_2$·2H$_2$O --.
Column 10, Line 49, "Na-citrate.2H$_2$O" should be -- Na-citrate·2H$_2$O --.
Column 10, Line 50, "CaCl$_2$.2H$_2$O" should be -- CaCl$_2$·2H$_2$O --.
Column 10, Line 53, "Na-citrate.2H$_2$O" should be -- Na-citrate·2H$_2$O --.
Column 10, Line 53, "CaCl$_2$.2H$_2$O" should be -- CaCl$_2$·2H$_2$O --.
Column 10, Line 56, "Na-citrate.2H$_2$O" should be -- Na-citrate·2H$_2$O --.
Column 10, Line 57, "CaCl$_2$.2H$_2$O" should be -- CaCl$_2$·2H$_2$O --.
Column 12, Line 14, "Na-citrate.2H$_2$O" should be -- Na-citrate·2H$_2$O --.
Column 12, Line 15, "CaCl$_2$.2H$_2$O" should be -- CaCl$_2$·2H$_2$O --.
Column 12, Line 23, "Na-citrate.2H$_2$O" should be -- Na-citrate·2H$_2$O --.
Column 12, Line 23, "CaCl$_2$.2H$_2$O" should be -- CaCl$_2$·2H$_2$O --.

Signed and Sealed this
Sixth Day of June, 2023

Katherine Kelly Vidal
*Director of the United States Patent and Trademark Office*